(12) United States Patent
May

(10) Patent No.: US 10,835,734 B1
(45) Date of Patent: Nov. 17, 2020

(54) HIGH AND LOW IMPEDANCE SYSTEMS AND METHODS FOR THE GENERATION AND USE OF CONSTANT INTENSITY ELECTRIC FIELDS

(71) Applicant: Wayne May, Pahrump, NV (US)

(72) Inventor: Wayne May, Pahrump, NV (US)

( * ) Notice: Subject to any disclaimer, the term of this patent is extended or adjusted under 35 U.S.C. 154(b) by 266 days.

(21) Appl. No.: 16/107,988

(22) Filed: Aug. 21, 2018

Related U.S. Application Data

(60) Provisional application No. 62/548,335, filed on Aug. 21, 2017.

(51) Int. Cl.
| | | |
|---|---|---|
| *C25B 9/00* | (2006.01) | |
| *A61N 1/04* | (2006.01) | |
| *A61B 18/14* | (2006.01) | |
| *A61N 1/32* | (2006.01) | |
| *A61N 1/39* | (2006.01) | |
| *A61B 18/00* | (2006.01) | |

(52) U.S. Cl.
CPC ............ *A61N 1/0416* (2013.01); *A61B 18/14* (2013.01); *A61N 1/327* (2013.01); *A61B 2018/00083* (2013.01); *A61N 1/39* (2013.01)

(58) Field of Classification Search
CPC ........ A61N 1/0416; A61N 1/327; A61N 1/39; A61N 1/0424; A61N 1/042; A61B 18/14; A61B 2018/00083; H05H 1/2406; H05H 2001/2456; G01N 27/44713
See application file for complete search history.

(56) References Cited

U.S. PATENT DOCUMENTS

| | | |
|---|---|---|
| 8,221,596 B2 | 7/2012 | May et al. |
| 8,226,811 B2 | 7/2012 | May et al. |

*Primary Examiner* — Xiuyu Tai
(74) *Attorney, Agent, or Firm* — FisherBroyles, LLP; Rob L. Phillips

(57) ABSTRACT

Disclosed are high and low impedance systems and methods for the generation and use of constant intensity electric fields for a variety of applications. Electric fields may be generated through gas, liquid, or solid phase materials for a variety of purposes on a subject material itself, or on materials, particles, or objects mixed, dissolved, suspended, or otherwise entrained in such materials, or on both. A number of systems and methods involve certain device geometries, parallel alignment of the electric field vector with the material under treatment, separation of the high impedance electrodes from the material under treatment, voltage or current sourcing linear and quasilinear voltage ramp input waveforms, and the employment of a high impedance dielectric coating on one side of conductive substrates of electrodes that function as barriers to electronic and ionic current.

12 Claims, 11 Drawing Sheets

140
141

HIGH AND LOW IMPEDANCE SYSTEMS AND METHODS FOR THE GENERATION AND USE OF CONSTANT INTENSITY ELECTRIC FIELDS

CROSS-REFERENCE

This application claims priority to U.S. Patent Application No. 62/548,335 filed Aug. 21, 2017 which is incorporated herein for all purposes.

FIELD OF THE INVENTION

The embodiments of the present invention relate to systems, methods, device geometries, and system element arrangements for the generation of electric fields through gas, liquid, or solid phase materials under treatment to achieve a range of desired electric field effects on subject materials, or objects entrained therein, or both.

BACKGROUND

In the context of this disclosure, a material under treatment of an electric field includes the gas, liquid, or solid phase itself, as well as any material, particle, or object dissolved, suspended, or otherwise entrained in that material. The acronym MUT will be used to refer to the Material Under Treatment, anything contained in that material, or both. The acronym HIE refers to High Impedance Electroporation detailed in U.S. Pat. Nos. 8,221,596 and 8,226,811 and which are both incorporated by reference herein and owned by the applicant hereof. The acronym PEF refers to traditional Pulsed Electric Field electroporation methods and devices of the prior art that employ bare metallic or electrically conductive electrodes. PEF methods and devices generate electric fields with low impedance electrodes and are always accompanied by electronic conduction current. The term "conduction current" refers to electronic and/or ionic current passing through electrically conductive electrodes, through the dielectric barriers that coat the electrodes of the embodiments of the present invention and the prior art related to HIE, or through the MUT. The terms "near zero" or "near absence" refer to a value insignificantly miniscule with respect to the same metric in other parts of an element, device, or system, or with respect to an absolute zero value, e.g., trivial conduction current versus no conduction current, diminutive electrochemical reactions versus no electrochemical reactions, etc. The term "high impedance" refers to the electrical impedance of conductive electrode substrates coated with dielectric material barriers, thereby largely forestalling conduction current due to high volume resistivity. High impedance is used to differentiate the embodiments of the present invention from the prior art that comprise bare metallic or otherwise electrically conductive electrodes that have low resistivity, and therefore low impedance. Said prior art includes but is not limited to methods and devices such as PEF electroporation, electric field flow fractionation (EFFF), heart muscle defibrillation, electrophoresis, electric field flow cytometry, electrochromatography, electric field molecular orientation, flocculation, demulsification (oil/water), electro-osmosis, tumor ablation, precipitation (stack gas particles for example), and many others. The term "barrier" when directed towards the embodiments of the present invention refers to the dielectric coating that covers the electrically conductive substrate of an electrode. The term barrier is used in deference to the barrier functions that the dielectric material provides, such as a barrier to electron and ion conduction from the electrically conductive substrate of the electrode to the MUT or vice versa. Depending on the embodiment, electrically conductive substrates of the electrodes described herein comprise gold, alloys of titanium and tungsten, silver, and other electrically conductive materials such as carbon.

The application of an electric field is useful in a variety of applications. For purposes of this disclosure, and for physics in general, an electric field is differentiated from an electric current which is either conduction current involving the movement of electrons or ions, or a displacement current defined as a time variant electric field. In the ideal case, a static or dynamic electric field can be formed, and can exist, through a material in the absence of electric conduction current, either electronic or ionic in nature. In practice, conduction current can never be limited to absolute zero value because all dielectric materials designed to forestall or mitigate conduction current conduct some electronic and/or ionic current, especially at nanoscale thickness. Electric fields are used for a variety of purposes, such as electroporation, storing energy or information in a capacitor, modification of power by the slow charge and fast discharge of energy from a capacitor, or as an electronic switch such as a transistor. In many of these applications, conduction current is undesirable because of deleterious effects caused by electronic or ionic current, e.g., the production of waste heat or electrochemical byproducts. The embodiments of the present invention are directed to applications that benefit from a reduction in conduction current, either electronic or ionic in nature, or both, while retaining the desired electric field effects. Electric field effects that benefit from reduced conduction current include lethal and nonlethal electroporation, cellular transfection, cellular extraction or insertion of molecules, electrophoresis, heart muscle defibrillation, electric field-flow fractionation, flocculation, field induced changes in phase, particle distribution, or temperature, and many others.

It would be beneficial in this field if methods for generating electric fields were developed that not only substantially reduce conduction current and its associated problems, but that also provide means to overcome the limitations imposed by the inverse correlation between dielectric breakdown strength and permittivity, as well as means to independently control field intensity versus field exposure time by design, engineering, or electronic techniques regardless of the electrical conductivity of the MUT, operating conditions, or applications that require both high intensity and long duration electric field exposure. The systems and methods disclosed herein achieve each of these objectives.

SUMMARY

The embodiments of the present invention involve high impedance systems and methods for generating constant intensity electric fields comprised of novel device geometries, novel arrangements of certain functional elements, and novel methods of electrically powering the electrodes with both current and voltage sourced linear and quasilinear input waveforms. In concert, the systems and/or methods provide the ability to generate electric fields through any material regardless of electrical conductivity for periods significantly longer than disclosed by the prior art systems and/or methods, provide engineering control over field intensity versus field exposure time by manipulating certain element dimensions, provide a means to use barrier materials that present low permittivity but high dielectric breakdown strength, or conversely, high permittivity but low breakdown strength by exploiting the arrangement of certain functional elements, scale in capacity over any range of process flow rates by providing independent engineering control over the area of the electrodes versus the dimensions of the MUT, and provide means to overcome limitations associated with fluids that have high electrical conductivity by manipulating electrode area, MUT length, or both. The systems and/or methods herein can be employed while retaining the ability to accomplish any electroporation or electric field effect of the type capable of or demonstrated in the field. The benefits and improved capabilities are accomplished while significantly mitigating certain limitations and constraints known in the prior art, such as the generation of deleterious and cytotoxic electrochemical byproducts, the generation of flammable/explosive oxygen and hydrogen gas (electrolysis), excessive Joule heating of the MUT, and aggressive electrode corrosion.

As with U.S. Pat. Nos. 8,221,596 and 8,226,811 the conductive substrates of the electrodes embodied herein are coated with a dielectric material to forestall electronic and ionic conduction current. The amplitude of electron conduction current that flows through the dielectric barrier is proportional to the applied voltage, barrier thickness, and volume resistivity. For ion conduction current, the amplitude is proportional to ionic conductivity, barrier thickness, and the local electrical field gradient. Dielectric barrier materials having high volume resistivity are selected, i.e., that are good electrical insulators, thus significantly reducing trans-barrier conduction current reducing electrochemical reactions and electrolysis of water. The embodiments of the present invention purposefully align the electric field vector parallel with the flow direction (when a fluid) or orientation (when a solid) of the MUT as detailed below whereas HIE purposefully aligns said vector perpendicular to the flow direction or orientation of the MUT. This difference is illustrated in FIGS. 1A versus 1B.

For the purposes of promoting an understanding of the principles in accordance with the embodiments of the present invention, reference will now be made to the embodiments illustrated in the drawings and specific language will be used to describe the same. It will nevertheless be understood that no limitation of the scope of the invention is thereby intended. Any alterations and further modifications of the inventive feature illustrated herein, and any additional applications of the principles of the invention as illustrated herein, which would normally occur to one skilled in the relevant art and having possession of this disclosure, are to be considered within the scope of the invention claimed.

The embodiments of the present invention utilize parallel alignment of the field vector with the flow direction of the MUT. The parallel field alignment enables the area of the electrodes of the system and methods to be manipulated without having to change the area of the MUT. Parallel field alignment with the MUT also enables the distance between the electrodes of the system and methods, dimension $d_s$ in FIG. 1A, to be manipulated without having to change the area of the MUT and without causing any change in electric field intensity within the MUT. Increasing the distance $d_s$ between the electrodes of an HIE device proportionally decreases field intensity, so a higher applied voltage is required to restore the original field intensity. Increasing distance $d_s$ between the electrodes of the embodiments of the present invention causes no change in field intensity, so increasing the applied voltage is not required. Parallel field alignment with the MUT also enables the area of the MUT to be manipulated independently from the area of the electrodes.

Equation (1) is introduced to mathematically illustrate variables associated with the methods of the embodiments of the present invention.

$$E_s t_r = \hat{\varphi}_a \frac{\varepsilon_d}{\sigma_s} \frac{A_d}{A_s} \frac{1}{2d_d} \tag{1}$$

where ($\overline{E}_s$) is field intensity developed through the MUT, ($t_r$) is input ramp period, ($\hat{\varphi}_d$) denotes peak voltage applied to the electrodes, ($\varepsilon_d$) is permittivity of the barrier material, ($\sigma_s$) is MUT conductivity, ($d_d$) denotes the thickness of the dielectric barrier, and ($A_d$) and ($A_s$) are the cross-sectional areas of the electrode and MUT, respectively. The expression on the right side of equation (1) defines the value for the product of field intensity ($\overline{E}_s$) and input ramp period ($t_r$) on the left side. All electric field effects are directly proportional to the combined effect of field intensity and field exposure time. Since field exposure time is directly proportional to input ramp period, equation (1) defines the extent to which said intensity and exposure time can be increased or decreased for any given configuration.

For example, still referring to equation (1), since the area of the cross-sections areas of the electrode ($A_d$) and the MUT ($A_s$) can be independently manipulated using the system and methods described herein, changing either area can be exploited to increase or decrease field intensity, field exposure time, or both. This independent engineering method is not possible with other systems because its parallel plate or cylindrical architecture always results in unity, i.e. $A_d/A_s=1$, so they cannot be independently manipulated. Note also in equation (1) that the term for the distance ($d_s$) between the electrodes 100 of FIG. 1A does not appear, therefore changing the length can increase field exposure time for any given flow rate through connecting tube 102 shown in FIG. 1A, without changing field intensity ($\overline{E}_s$).

Independent design control over the area of the electrodes versus the area of the MUT also provides a means to compensate for dielectric barrier materials having low permittivity because system capacitance is proportional to electrode area. The method also provides independent control over field exposure time without affecting field intensity. This is so because field exposure time is directly proportional to system capacitance, viz. the $2^{nd}$ term on the right side of equation (1), and capacitance is directly proportional to electrode area ($A_d$) as shown in the numerator of the $3^{rd}$ term on the right side of equation (1). Since $A_d/A_s$ always equals 1 for the parallel architecture of HIE shown in FIG. 1B, these methods are not possible with the prior art of HIE. The embodiments of the present invention are useful for employing dielectric barrier materials that have low permittivity, but otherwise have desirable material properties such as food safety, high volume resistivity, high dielectric breakdown strength, or resistance to cleaning chemicals.

For the manifold barrier architecture of the embodiments of the present invention as depicted in FIG. 1A, engineering control can be exercised over the cross-sectional area of the conveying tube 102, term ($A_s$) in equation (1), while not having to change electrode area, term ($A_d$) in equation (1). Consequently, when treating materials with high electrical conductivity ($\sigma_s$), the diameter of tube 102 can be decreased, thus proportionally decreasing fluid area ($A_s$) to decrease MUT embodiments of the present invention provide means to compensate for materials under treatment that have high electrical conductivity, such as fruit juice, bract-water, municipal waste water, blood, wine, milk, etc.

Another embodiment of the present invention involves exercising engineering control over electrical resistance of the MUT in another manner, again without affecting field intensity or field exposure time. This is useful for employment of dielectric barrier materials that may have low volume resistivity, which causes more conduction current to flow for any given applied voltage, and therefore the generation of more undesirable electrochemical byproducts, but otherwise have desirable material properties such as high permittivity, high breakdown strength, good food safety, or resistance to sanitation chemicals and processes. This embodiment is accomplished by modifying the length ($d_s$) of the conveyance tube 102 or space for a solid MUT, which can be done without affecting field intensity because tube length can be varied without having to change electrode area ($A_d$), tube area ($A_s$), or barrier thickness ($d_d$). Since MUT resistance is directly proportional to tube length ($d_s$), and conduction current through the dielectric barrier material is proportional to said resistance, independent design control over tube 102 length ($d_s$) provides a means to compensate for dielectric barrier materials that have low volume resistivity. Increasing the distance between the parallel plates or coaxial cylinders of an HIE device requires an increase in the voltage applied to the electrodes to maintain the desired field intensity (the same applied potential over a greater distance results in lower volts/meter, therefore lower field intensity). For the embodiments of the present invention, system displacement current remains the same when tube length ($d_s$) is increased or decreased, but due to the corresponding increase or decrease in MUT resistance, the voltage drop across the MUT increases or decreases proportionally. Since the increase in voltage drop is consistent with and proportional to the increase in MUT length ($d_s$), field intensity remains the same and is unaffected.

For the methods of high impedance generation of electric fields (HIE), the electric field generated in the MUT is necessarily transient with respect to time, or time variant when driven by a time variant input signal, a sinusoidal input waveform for example. This is so because the parallel electrodes consistent with HIE methods form a series capacitive network separated by an electrically resistive element, either a gas or liquid phase fluid, or a solid MUT. The resistive element conveys electrons and ions from one electrode to the other, thus comprising a conduction current element within a displacement current network as shown in FIG. 2. Given the high impedance and low applied voltage of HIE devices, electronic conduction current is significantly limited, the extent of which is proportional to the volume resistivity of the dielectric barrier material. This in turn limits deleterious electrochemical byproducts and electrode corrosion, novel benefits with respect to HIE. Since the electrical conductivity of many materials treated with electric fields is high, such as juice, milk, or wine, a fast rise-time square-wave input is required to achieve the peak field intensity sufficient to cause biologic effects, pasteurization or transfection for example. FIG. 3 shows a time course graph 118 of the two field pulses generated through the MUT in response to a square waveform input pulse for an HIE device. Note that a peak field intensity is rapidly achieved, followed by the exponential decay of that field. Field exposure time for these two pulses is too short for some electroporation applications such as pasteurization of liquid foods.

Applicant has learned through microbiological experiments and electrical experiments and measurements that HIE methods are limited with respect to field exposure time, a critical counterpart of the high field intensity required for many electric field effects, notably lethal electroporation of bacteria suspended in liquid foods for pasteurization. Since field exposure time is directly proportional to device time constant of an HIE device, and since the use of dielectric barrier materials with high permittivity is the only option for increasing device time constant for an HIE device, an extensive search was conducted to identify dielectric materials that have both high breakdown strength and high permittivity. During this unsuccessful search, it was further learned that an inverse correlation between dielectric permittivity and breakdown strength existed for virtually all dielectric materials, especially materials like metal oxide ceramics that are suitable for many electric field effect applications. FIG. 4 illustrates a graph 125 of this relationship, indicating the inverse correlation that approximates $E_{bd} \propto \kappa^{-0.64}$ (black plot line), where ($E_{bd}$) denotes breakdown strength (field stress or time dependent), and $\kappa$ is relative permittivity (dielectric constant). Within a dielectric barrier's performance envelope, device time constant and thus field exposure time can be improved for HIE devices, but this requires thinner dielectric barriers, which lowers the peak voltage that can safely be applied to the barrier, which in turn lowers peak field intensity. With HIE, increasing both field exposure time and peak field intensity is not possible by dielectric material selection alone.

The embodiments of the present invention overcome HIE shortcomings via the application of current or voltage sourcing linear and quasilinear input ramps which represent a substantive improvement in field exposure time over HIE methods by generating a constant intensity electric field as opposed to a transient exponentially decaying field. In addition, the intensity and period of said constant intensity fields are not dependent on device time constant as with HIE, but rather are determined by the slope and peak voltage of the input voltage ramp.

In one embodiment of the present invention, a linear voltage ramped input waveform is employed. The input waveform in this embodiment is linear with respect to time, i.e., $dv/dt=m$, where m is a constant. In this configuration, the electrical response through the MUT begins with an exponential period, during which the capacitive barriers are charging, followed by a relatively long period constant amplitude displacement current which generates a long period constant intensity electric field. Electrical response for this configuration is shown in FIG. 5 as three voltage v. time plots: 1) input voltage ramp (plot line 130), 2) the MUT response (plot line 131), and 3) dielectric barrier response (plot line 132). The voltage drop across the MUT (plot line 131) follows the same time course as the electric field developed through the MUT, hence FIG. 5 illustrates the long period constant field intensity characteristic of the embodiments of the present invention versus the short period exponentially decaying field consistent as shown in FIG. 3. The embodiments of the present invention can increase field exposure time by factors of 100 to 10,000 times greater (or more) than conventional systems and/or methods (e.g., HIE, PEF, EFFF, electrophoresis, electroosmosis systems, electrochromatography, and others) depending on the electrical properties of the MUT and certain operating conditions.

In one embodiment of present invention, a quasilinear voltage ramp input is employed. The input waveform in this embodiment is quasilinear, incorporating an exponentially changing voltage element, which is the last term on the right side of equation (2):

$$\varphi_a(t) = \frac{\hat{\varphi}_a}{t_r}t + \frac{I}{C_t}te^{-t/\tau}$$

where ($\varphi_a$) and ($\hat{\varphi}_a$) denote applied voltage on time and peak ramp voltage respectively, ($t_r$) is ramp period, (t) is time, (I) is displacement current, ($C_t$) is total system capacitance, and ($\tau$) denotes device time constant. The input ramp slope in this embodiment is $dv/dt=m+A\cdot e^{-t/\tau}$, where A is determined by the quotient of displacement current over system capacitance. In this configuration, the electrical response through the MUT begins with a fast rise time peak field, during which the capacitive barriers are rapidly charging, followed by a quasi-constant intensity electric field which quickly decays towards the asymptote of a constant intensity electric field, i.e., where the input ramp slope m is constant. Electrical response for this configuration is shown in FIG. 6 as three voltage v. time plots: 1) input voltage ramp (plot line 136), 2) MUT response (plot line 137), and 3) dielectric barrier response (plot line 138). The voltage drop across the MUT (plot line 116) follows the same time course as the electric field developed through the MUT; hence FIG. 6 illustrates the long period constant field intensity character of the embodiments of the present invention versus the short period exponentially decaying field character as shown in FIG. 3. The embodiments of the present invention in this configuration can increase field exposure time by factors of 100 to 10,000 times greater (or more) than the conventional systems and/or methods depending on the electrical properties of the MUT and certain operating conditions. One advantage of current sourcing versus voltage sourcing the embodiments of the present invention is that the former generates longer constant intensity field periods than the latter, e.g., 768 μs versus 685 μs for the examples illustrated in FIGS. 5 and 6. However, current sourcing achieves longer field periods at the expense of shorter dielectric barrier service life. Current sourcing applied to high or low impedance devices for generating electric fields is novel for systems including HIE, PEF, EFFF, electrophoresis, electro-osmosis, electrochromatography, and others.

The embodiments of the present invention seek to generate constant intensity electric fields through (in) a MUT as opposed to a transient exponentially decaying electric field consistent with the prior art. Many electric field effects, including electroporation, can benefit from the combination of high field intensity and long field exposure time. Constant intensity field generation for the embodiments of the present invention is accomplished by action of input waveforms in the form of current or voltage sourcing linear and quasilinear voltage ramps, which are novel to the prior art.

The embodiments of the present invention also seek to substantially increase field exposure time over that consistent with the prior art, without affecting or diminishing field intensity. Said relatively long period exposure times can be further increased by increasing the area of the electrodes, which can be accomplished without having to change the cross-sectional area of the MUT. This independent engineering control method is enabled by the parallel alignment of the electric field vector with the flow direction or orientation of the MUT and separating the electrodes with a conveyance tube 102 or space.

The embodiments of the present invention also seek to compensate for dielectric barrier materials that have low volume resistivity instead of having to select dielectric materials with higher volume resistivity, which is a constraint for the methods of the prior art in terms of the availability and suitability of dielectric materials to perform diverse barrier and safety functions. Employment of low volume resistivity dielectric materials for methods of the prior art increases conduction current, which in turn increases deleterious electrochemical byproducts such as peroxides. For the embodiments of the present invention, this independent engineering control method is accomplished by increasing the length of the tube 102 connecting the flow manifolds A and B or the space for a solid MUT, as shown in FIG. 1A, which can be accomplished without having to change the area of the electrodes or the area of the MUT, and therefore without affecting field intensity or field exposure time.

The embodiments of the present invention further seek to compensate for dielectric barrier materials that have low permittivity instead of having to select dielectric materials with higher permittivity, which is a constraint for methods of the prior art because dielectric materials with high permittivity and high breakdown strength do not currently exist (see, FIG. 4). Employment of low permittivity dielectric materials for the methods of the prior art decrease both peak field intensity and field exposure time, which in turn decreases the effectiveness of any electric field effect. For the embodiments of the present invention, this independent engineering control method is accomplished by increasing the area of the electrodes, which can be done without having to change the area or length of the MUT, and therefore exposure time can be increased without diminishing field intensity.

The embodiments of the present invention further seek to compensate for dielectric barrier materials that have low breakdown strength instead of having to select materials with higher breakdown strength, which is a constraint for methods of the prior art because dielectric materials with high breakdown strength and high permittivity do not currently exist (see, FIG. 4). Employment of low breakdown strength dielectric materials for the methods of the prior art limit peak applied voltage to the electrodes, which limits the maximum field intensity that can be generated, which in turn decreases the effectiveness of any electric field effect. For the embodiments of the present invention, this engineering control method is accomplished by increasing dielectric barrier thickness and proportionally increasing the area of the electrodes, which can be accomplished without having to change the area or length of the MUT, and therefore without diminishing field intensity or field exposure time.

Other variations, embodiments and features of the present invention will become evident from the following detailed description, drawings and claims.

DETAILED DESCRIPTION

As will be appreciated by one skilled in the art, aspects of the present invention may be embodied as a system and method. Accordingly, aspects of the embodiments of the present invention my use hardware only or hardware combined with software.

The systems and methods of the present invention utilize a concert of device geometries, arrangements of functional elements, engineering control methods, and input waveforms powering the same. Although the consummate benefits and advantages of the embodiments of the present invention are fully realized when all disclosed techniques, geometries, and arrangement of elements are employed in the methods herein, any single said technique, geometry, or arrangement represents a substantive advantage over the prior art of Pulse Electric Field methods and devices for electroporation (PEF), High Impedance methods for Generating Electric Fields (HIE) and other electric field effect methods such as Electric Field Flow Fractionation, Heart Muscle Defibrillation, Electrochemotherapy, Dielectric Electrophoresis, Electric Field Demulsification or Flocculation, Electro-osmosis, Electric Field Tumor Ablation, Field Flow Cytometry, Electrochromatography, and others. Without exception, said prior art pertaining to electric field effects, and many others, employ electrically conductive electrodes, e.g., bare metal, electrodes coated with electrically conductive materials, or conductive carbon electrodes to generate electric fields, said electrodes comprising a series resistive network with the MUT. By contrast, the embodiments of the present invention use high impedance methods to generate electric fields, employing electrically conductive substrates that are coated with a dielectric material, i.e., an electric insulating material, said electrodes comprising a series capacitance network with the MUT.

The embodiments of the present invention are directed to applications that benefit from reduced conduction current for any given field intensity or field exposure time that are employed to cause an electric field effect, as well as towards HIE that operates with near zero conduction current, but is limited to the generation of high intensity fields for short periods of time, or conversely, the generation of low intensity fields for long periods of time.

Figure 1A:
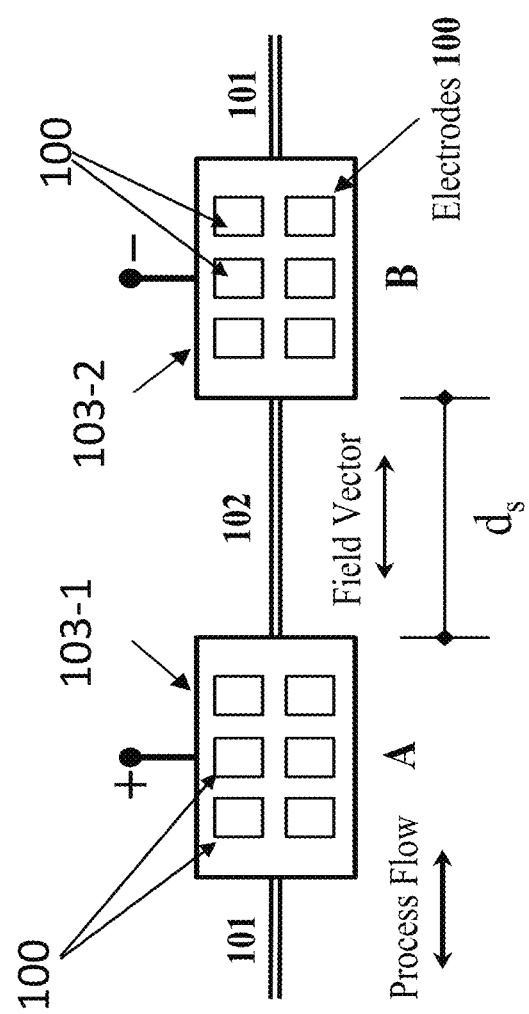
FIG. 1A illustrates a block diagram of system of the type which may be used with the embodiments of the present invention.
Figure 1B:
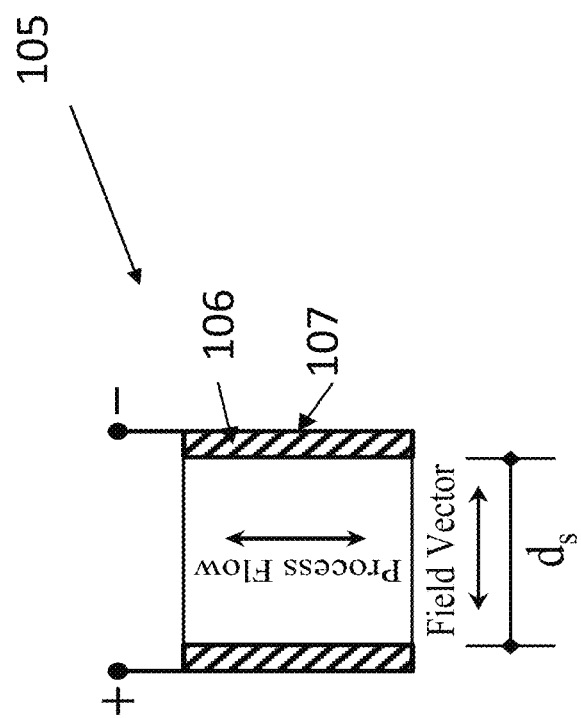
FIG. 1B illustrates a block diagram of a system of the prior art.

Referring to FIG. 1A, the positive A and negative B polarity electrodes are flow manifold configurations comprised of one or more electrodes 100 or electrode modules (used interchangeable hereinafter), and a fluid pathway parallel 101 to the manifolds A or B (103-1, 103-2) and the electrodes 100 housed in or attached therein. An electrode module may consist of any number of individual electrodes 100. Regardless of material phase (e.g., gas, liquid, or solid), the MUT comes into direct physical contact with the dielectric barriers coating the conductive substrates of electrodes 100 within both flow manifolds A and B. One or more electrodes 100 that are housed or attached within each flow manifold A and B can be arranged in a parallel, coplanar, interdigitated, dihedral, or any geometry provided that two conditions are achieved by the configuration of the flow pathway or space with respect to the electrodes 100: 1) the electrodes 100 make or otherwise form a series capacitive network with the MUT, and 2) the electric field vector generated by action of the applied linear voltage ramp and the electrodes 100 is parallel with/to the flow direction if a fluid or the orientation if a solid MUT. FIG. 1B shows a prior art HIE system 105 with a dielectric barrier 106 and conductive substrate 107 through which a fluid flows.

Figure 2:
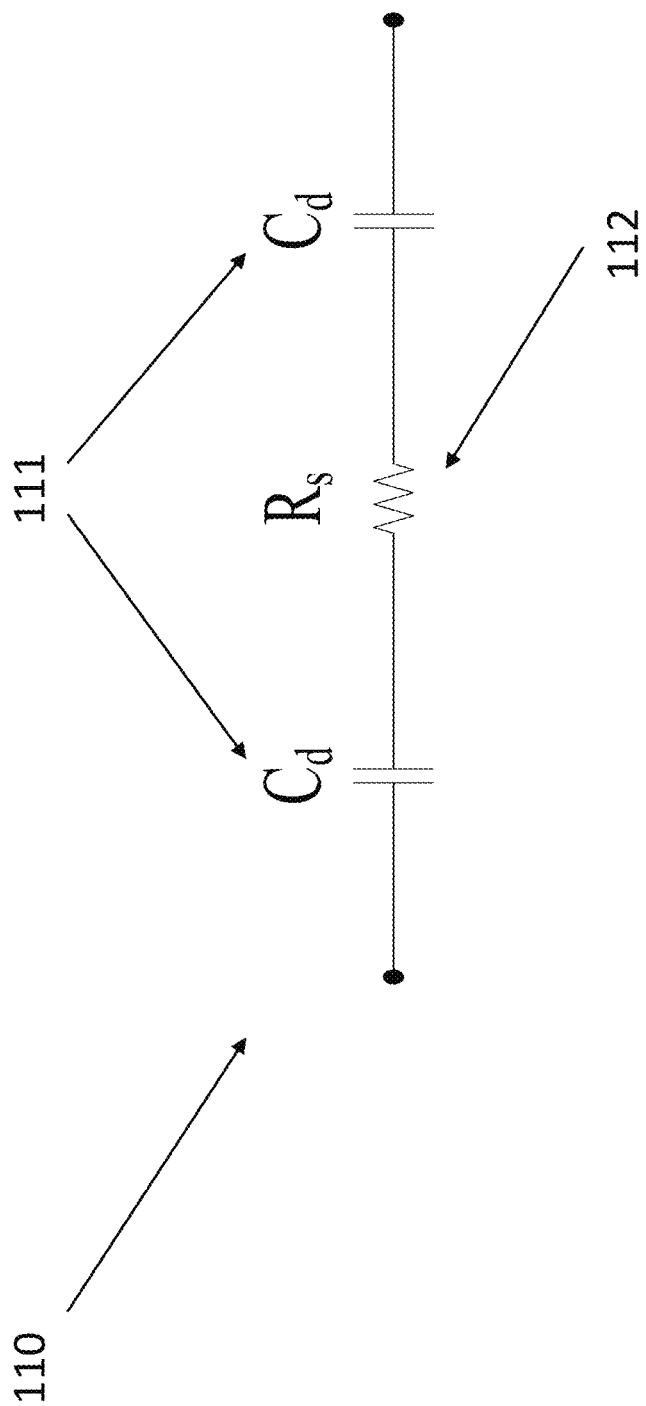
FIG. 2 illustrates a block diagram of a prior art HIE circuit.

Other geometric configurations of the electrodes 100 relative to the flow manifolds A and B are possible provided that they are so arranged as to comprise or otherwise form a series capacitance network with the MUT and the electric field vector is made parallel to said flow direction or solid orientation of the MUT. For example, electrodes 100 can be configured in a coplanar geometry by stacking electrodes 100 coaxially, around a central rod for example serving as an electrical connection for all stacked electrodes 100. Such a configuration comprises or forms a series capacitive network with the MUT, as well as achieving a parallel alignment of the field vector with said flow direction or solid orientation of the MUT. The geometric configuration of the electrodes 100 in one flow manifold A with respect to the other flow manifold B are still coplanar in this configuration because each electrode 100 in one flow manifold resides (is positioned) on the same plane as its counterpart electrode 100 in the other flow manifold A or B. The distinction between said geometric configurations versus the prior art of HIE is that with the embodiments of the present invention the electric field vector is aligned parallel with/to the MUT, whereas the electric field vector of the prior art HIE is aligned perpendicular with/to the MUT. An equivalent electrical circuit 110 for the embodiments of the present invention and the prior art is illustrated in FIG. 2 where capacitors ($C_d$) 111 account for the electrical capacitance of the dielectric barriers' coating the conductive substrates of electrodes 100, and resistor ($R_s$) 112 accounts for the electrical resistance of the MUT flowing through the connecting tube 102 if in gas or liquid phase, or occupying a space between manifolds A and B if in solid phase. The area of one, some, or all of electrodes 100 can be changed to increase or decrease device capacitance, which in turn increases or decreases field intensity or field exposure time depending on the goal. Another engineering control method separate from the method of changing the area or number of the electrodes 100 is independently changing the slope or the peak applied voltage of the input linear voltage ramp, one versus the other, thereby controlling field intensity versus field exposure time within the performance envelope established by the electrode area, barrier permittivity, and barrier thickness. The area of electrodes 100 can also be changed to compensate for low permittivity or low breakdown strength dielectric barrier materials that coat the conductive substrate of each electrode 100.

When treating (processing) a fluid in gas or liquid phase, it may enter the system at the inlet of either positive A or negative B polarity flow manifolds via the fluid conveyance tube 101, then through conveyance tube 102 connecting the two flow manifolds A and B, and then through the opposite polarity flow manifold A or B depending on flow direction. By action of a linear or quasilinear input voltage ramp powering the system and the capacitive reactance of the electrode barriers, a displacement current is generated, which conducts as ionic current through the MUT flowing within connection tube 102 or said space between the electrodes 100. The length of the connecting conveyance tube 102 is distance ($d_s$) illustrated in FIG. 1A. Due to the electrical resistance of the MUT and said ionic current, a voltage drop develops across the MUT that is proportional to its area ($A_s$) and length ($d_s$), which is the same as the area and length of the connection tube 102. This voltage drop is manifested as an electric field, the intensity of which is said voltage drop divided by said length ($d_s$). This is the electric field that produces the electric field effects subject the embodiments of the present invention.

A further engineering control method is changing the length of the connecting tube 102 to change field exposure time. A longer tube length, for example, increases field exposure time for any given flow rate, electrode area, system displacement current, barrier permittivity, or barrier thickness without having to change the area of the electrodes 100, dielectric barrier thickness, area of the connecting tube 102, i.e., the area of the MUT, or the peak applied voltage. A further engineering control method is changing the area of connecting tube 102 to change field intensity. A smaller tube area, for example, increases field intensity for any given system displacement current, electrode area, barrier permittivity, or barrier thickness without having to change any element dimension or operating conditions as cited above.

In the case were a solid phase MUT is being treated or processed, conveyance tubes 101 and 102 are not required, and connecting tube 102 is replaced by a space that contains the MUT, either side of which is in direct contact with the dielectric barriers of the electrodes 100 in such a manner that the area of the electrodes 100 can be manipulated by design without having to change the contact area between the electrodes 100 and the solid MUT, for example by means of an ionically conductive gel, an ion permeable membrane, or other suitable materials. The flow manifolds A and B are also not required when treating a solid phase MUT. In this configuration, a fractional portion of the area of the dielectric coating on the electrodes 100 is made to, or placed in, direct physical contact with the solid MUT by an ionically conductive or ion permeable material. Said arrangement of functional elements can be configured to treat or otherwise cause an electric field effect in a cancerous tumor for DNA or drug infusion by means of electroporation, heart muscle for defibrillation by action of interrupting chaotic rhythm by means of an electric field (this action is not caused by conduction current), in-vivo or ex-vivo tissue permeabilization for DNA or drug therapy, gel or cellulose acetate electrophoresis by means of field effected ion mobility and/or permeation, hair removal by means of electrolysis, and others. One example for arranging said functional elements is defibrillation of heart muscle or electrochemotherapy of brain tumors where the electrodes 100 are configured as surgical paddles with a contact surface area comprised of an ion conducting material such as an elastomer membrane that can be positioned on either side of said muscle or tumor. In these examples, and many other applications, an electric field effect can be attained by the embodiments of the present invention without the deleterious effects of conduction current, such as burning the contact surface of the tissue being treated, over heating the tissue or tumor, or the infusion of cytotoxic agents generated by electrochemical reactions such as peroxide, all of which are common problems and constraints of the prior art.

The recited engineering control methods, systems, device geometries, and arrangements of functional elements collectively and separately provide means to manipulate the electrical behavior and subsequent performance of the embodiments of the present invention to suit virtually any material to be treated, at any field intensity or exposure time required, to achieve any desired electric field effect that would benefit from near zero conduction current, near zero production of electrochemical byproducts, and in the complete absence of electrode corrosion, which together, represent limitations, constraints, and safety hazards consistent with the prior art.

Figure 3:
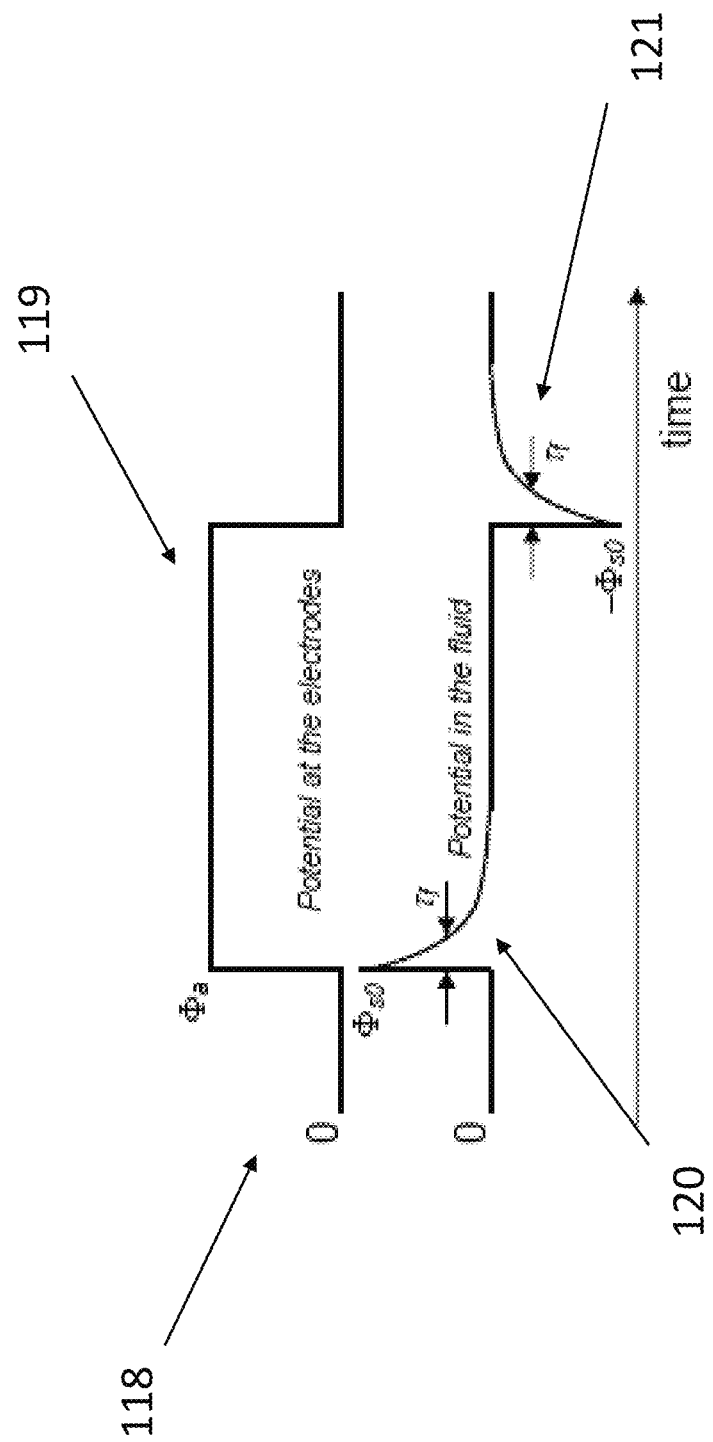
FIG. 3 illustrates a fast rise time square input waveform versus two exponentially decaying voltage/field response waveforms.

FIG. 3 shows a time course graph 118 of the two field pulses generated through the MUT in response to a square waveform input pulse for an HIE device. More specially, FIG. 3 shows a fast rise time square input waveform 119 versus two exponentially decaying voltage/field response waveforms 120, 121. Note that a peak field intensity is rapidly achieved, followed by the exponential decay of that field. Field exposure time for these two pulses is too short for some electroporation applications such as pasteurization of liquid foods.

Figure 4:
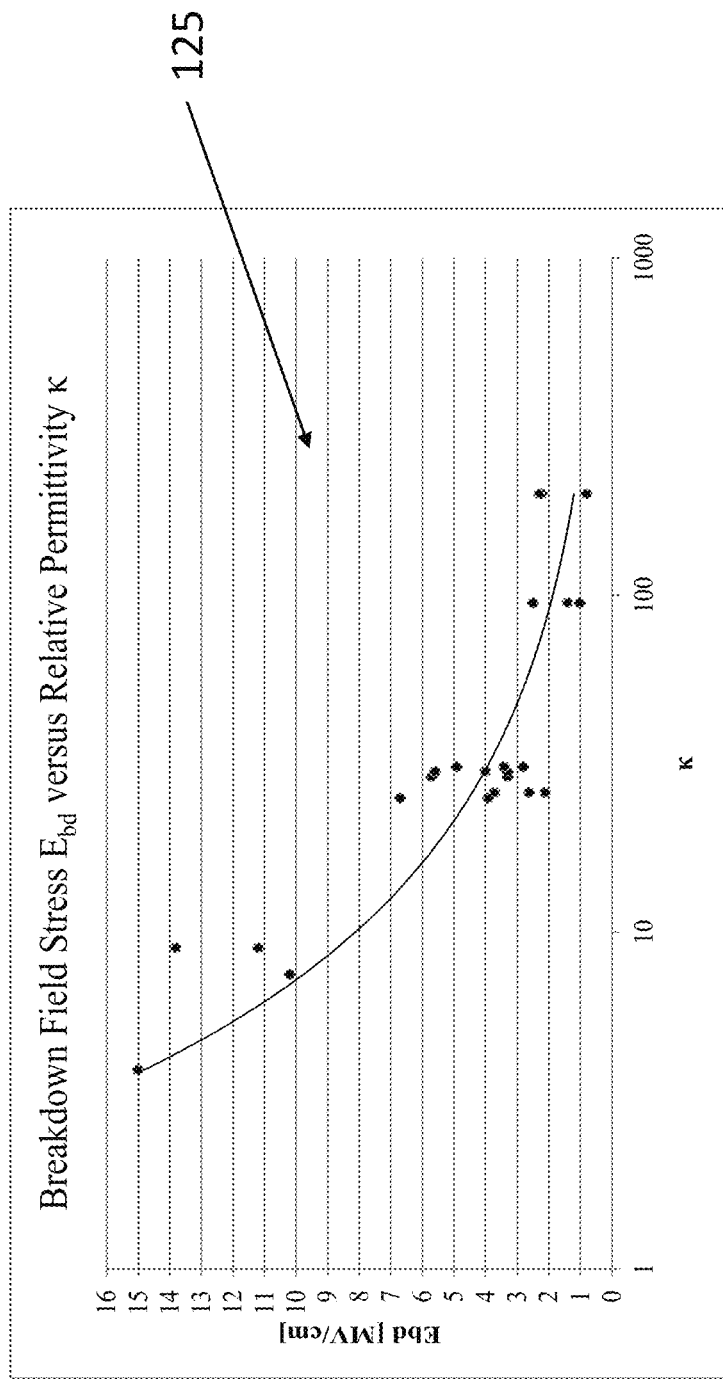
FIG. 4 illustrates a graph detailing dielectric material breakdown strength (field stress, not time dependent) versus relative permittivity for a range of diverse dielectric materials.
Figure 5:
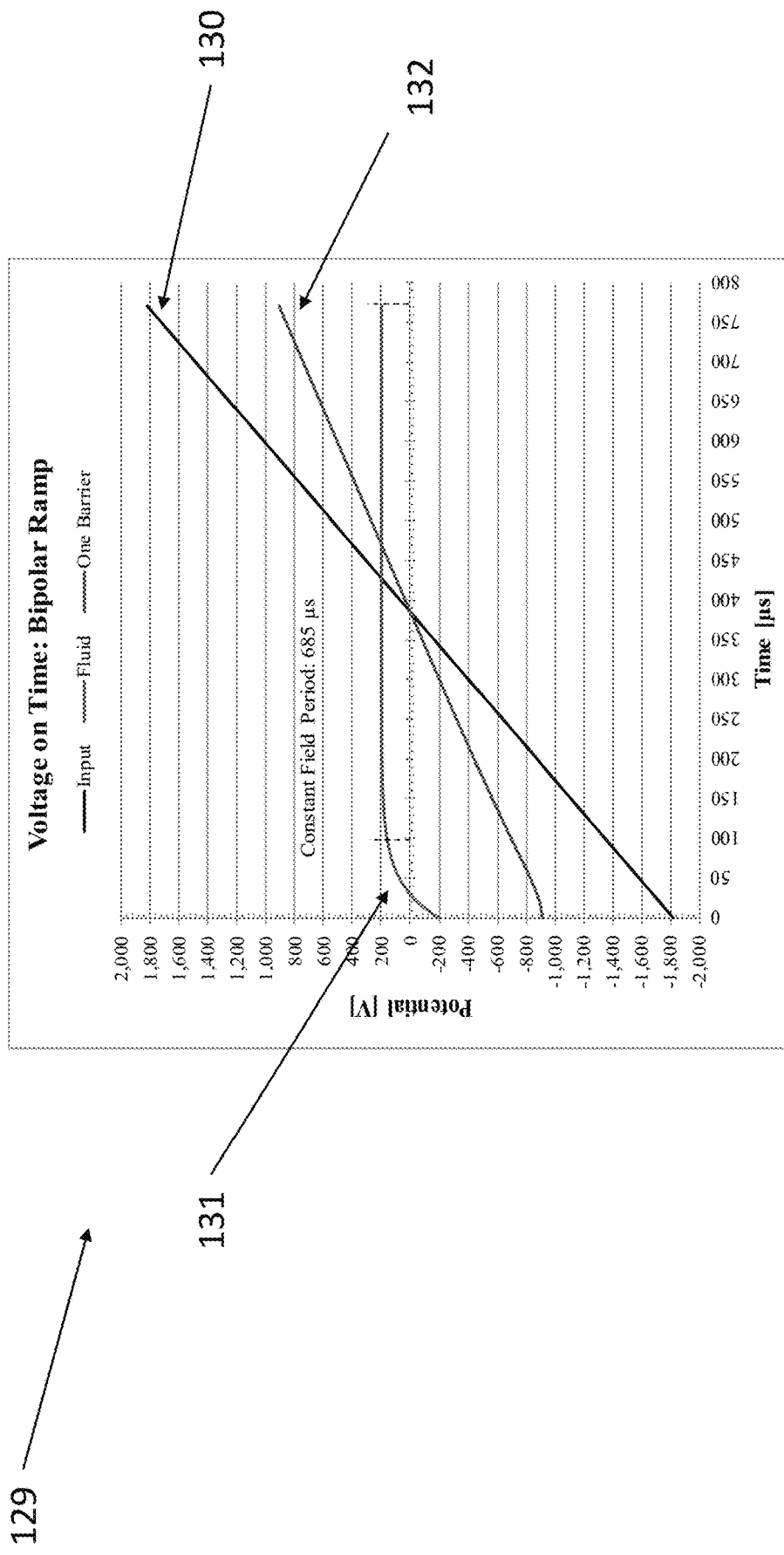
FIG. 5 illustrates a graph detailing the electrical response when voltage is sourced by a linear voltage ramp waveform according to the embodiments of the present invention.
Figure 6:
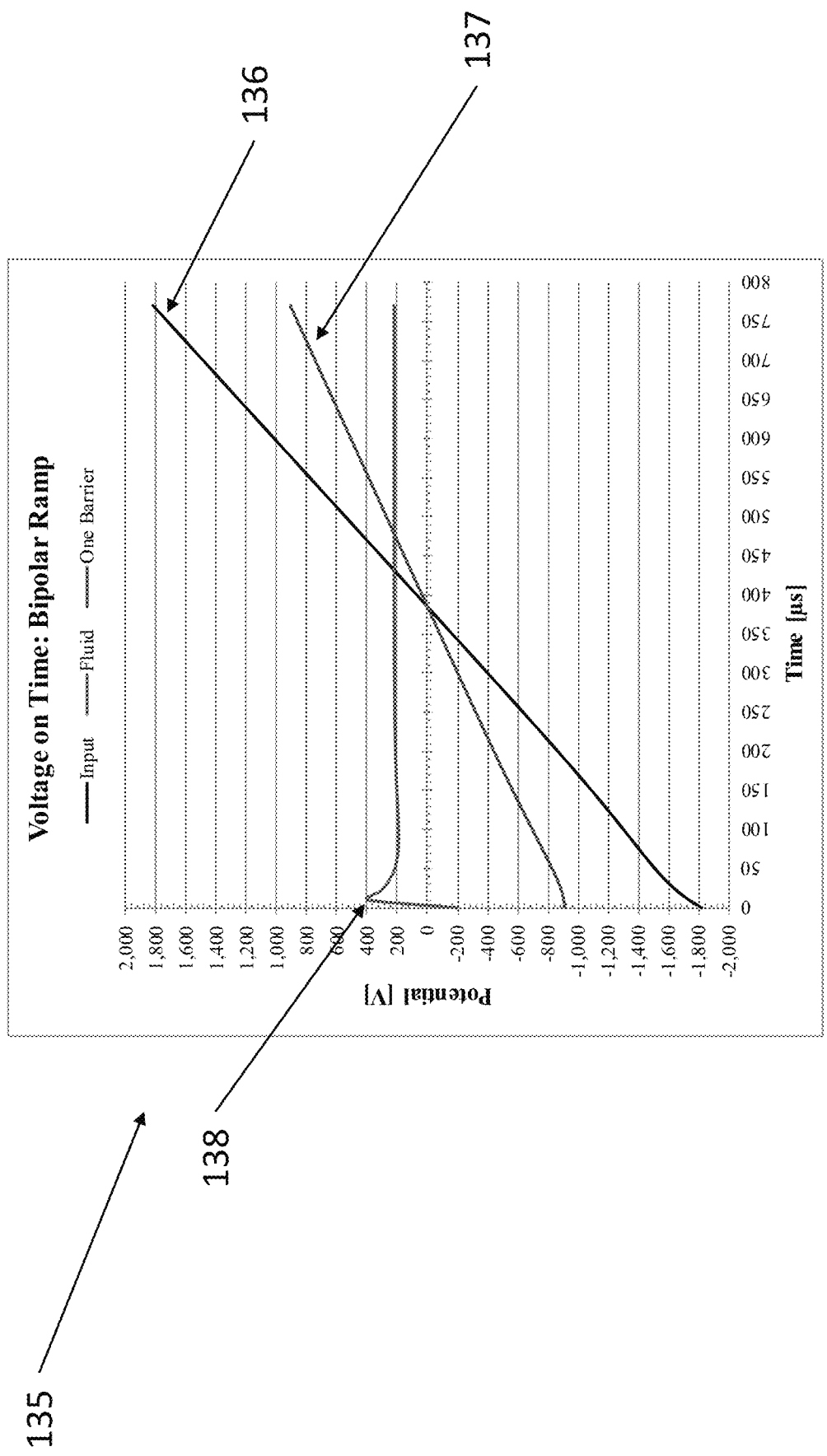
FIG. 6 illustrates a chart detailing the electrical response when voltage is sourced by a quasilinear voltage ramp waveform according to the embodiments of the present invention.

FIG. 4 shows a graph 125 detailing dielectric material breakdown strength (field stress, not time dependent) versus relative permittivity for a range of diverse dielectric materials. FIG. 5 shows a graph 129 detailing the electrical response when voltage is sourced by a linear voltage ramp waveform according to the embodiments of the present invention. The graph 129 depicts input voltage ramp 130 along with the MUT response 131 and dielectric barrier response 132 to the applied voltage. FIG. 6 illustrates a graph 135 detailing the electrical response when voltage is sourced by a quasilinear voltage ramp waveform according to the embodiments of the present invention. The graph 135 depicts input voltage ramp 136 along with the MUT response 137 and dielectric barrier response 138 to the applied voltage.

Figure 7:
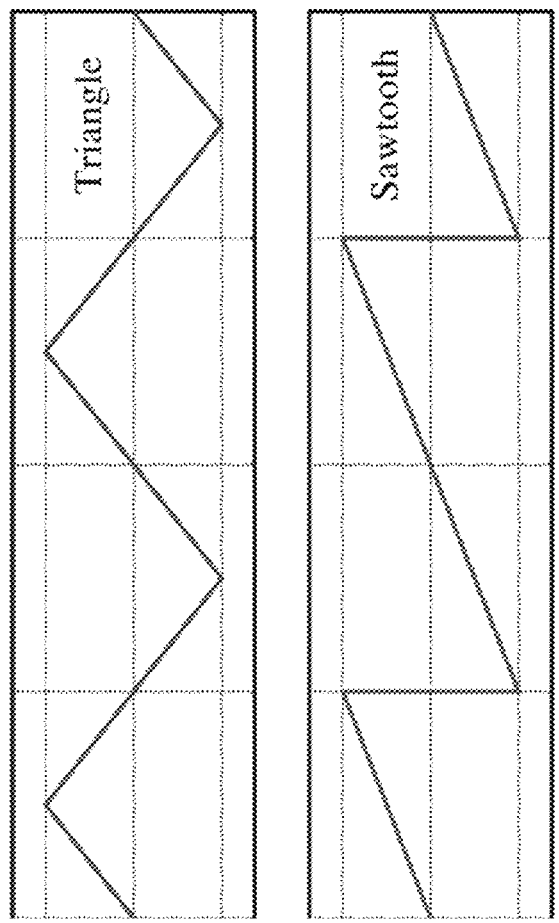
FIG. 7 illustrates charts detailing two voltage sourcing linear voltage input waveforms of the type usable with the embodiments of the present invention.

FIG. 7 illustrates two configurations of linear voltage ramp input waveforms suitable for use with the embodiments of the present invention: (i) a bipolar triangle waveform 140, and (ii) a bipolar sawtooth waveform 141. The vertical axis is applied electric potential in volts (no scale), the horizontal axis is time (no scale and common to both waveforms shown). As with all electrical networks that are dominated by capacitive reactance, including the embodiments of the present invention, powering capacitive electrodes with a linear voltage ramped input generates a constant amplitude displacement current after the capacitive elements in the system have charged or discharged. The applied voltage of a linear voltage ramp increases at a constant rate with respect to time, meaning that the ramp has a constant slope, i.e., $dv/dt=m$ where m is a constant. FIGS. 5 and 6 illustrate two linear voltage ramp input waveforms 130, 136, the former comprising a voltage sourcing ramp, the latter comprising a current sourcing ramp. FIGS. 5 and 6 also illustrate the time course of the voltage developed across the MUT 131, 137, which mirrors the time course of system displacement current when the electrical resistance of the MUT is constant, viz. after thermal equilibrium has been reached in the MUT. System displacement current also mirrors the time course of the electric field generated through (in) the MUT after thermal equilibrium has been reached.

Figure 8:
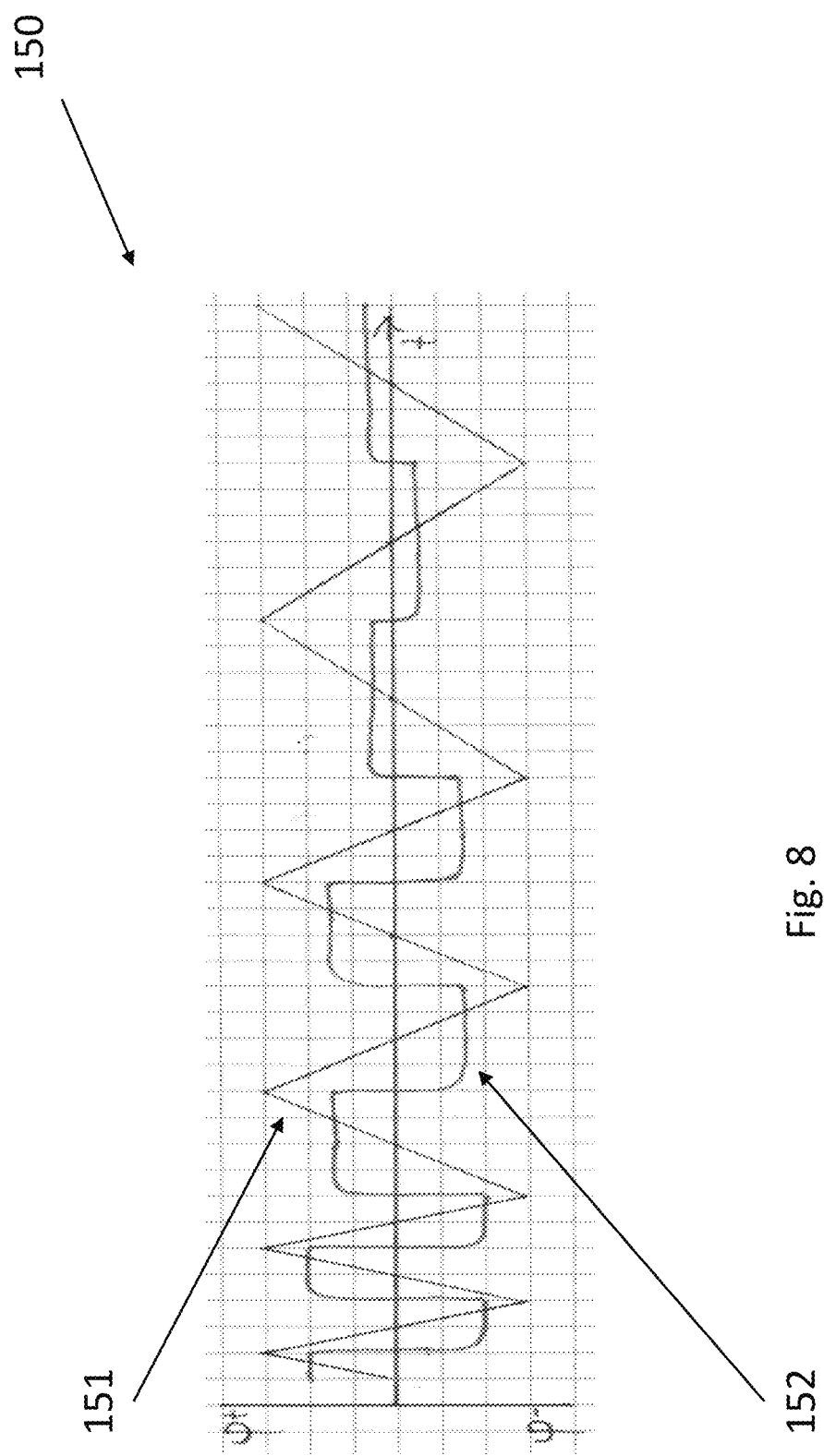
FIG. 8 illustrates a chart detailing a progressively sloped linear voltage ramp input waveform of the type usable with the embodiments of the present invention.

A number of other voltage and current sourcing linear voltage ramped input waveforms can be configured, all generating a constant intensity electric field having some period through the MUT. Different waveform configurations produce different electric field effects and can be used to tailor field effects for higher performance depending on the electrical characteristics of the MUT and operation conditions. For example, targeting a particular species of cellular organism, to increase the rate of DNA or drug infusion into a somatic cell or tumor or to increase or target the extraction of commercially valuable molecules from yeast, heart muscle defibrillation, etc. Unipolar linear voltage ramp waveforms can also be employed in cases where such waveforms are known to increase a desired electroporation effect, for example to control the rate of electrophoresis or selectiveness of electro-osmosis, and many other applications. Some examples of alternate waveforms that retain the ability to generate constant intensity electric fields are progressive slope types, either increasing slope or decreasing slope from one wave segment (ramp) to the next, compound J type waveforms (not illustrated), and others. FIG. 8 illustrates a graph 150 of one type of waveform in the form of a progressively sloped linear voltage ramp input waveform 151. The input waveform 151 begins with a steep slope on the left, after which the slope gradually decreases from one ramp section to the next in succession with respect to time. The plot line maps the time course of the voltage developed across the MUT 152, which mirrors the time course of the electric field developed through (in) the MUT. Note that the amplitude of the constant intensity field is high at the beginning of the input signal on the left, and then progressively decreases with time, while the duration of the constant intensity field progressively increases with respect to time. The vertical axis is applied voltage or MUT field intensity, the horizontal axis is time.

Figure 9:
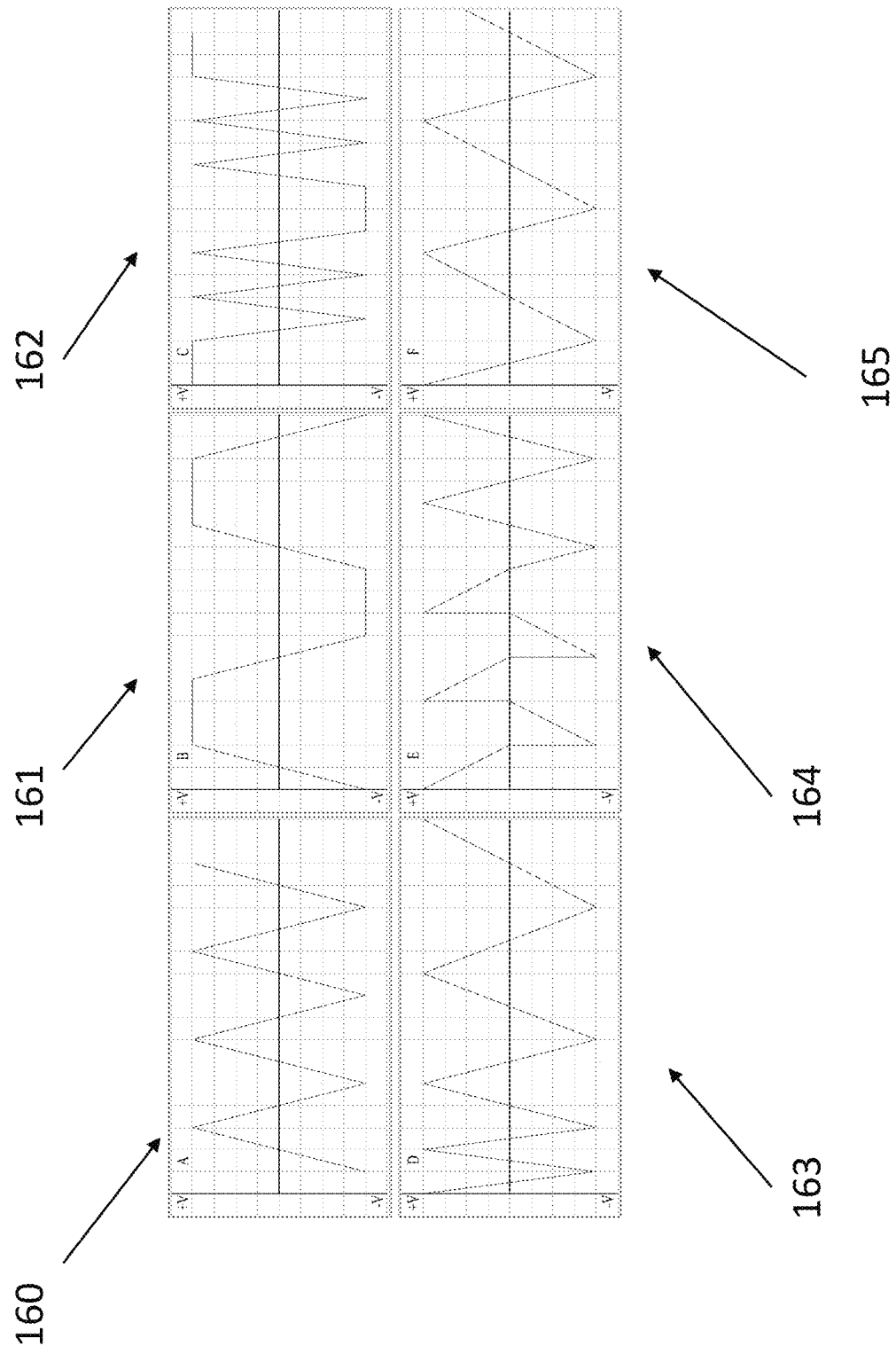
FIG. 9 illustrates charts detailing different linear voltage ramp input waveforms of the type usable with the embodiments of the present invention.

A number of other input waveforms can be configured to increase the performance or tailor the effect of the embodiments of the present invention, such as by example the configurations illustrated in the graphs 160-165 of FIG. 9, each one generating a different constant intensity electric field in terms of amplitude and duration configured to be more effective with respect to the electrical characteristics of a MUT, a particular organism or tissue, or a particular operating condition.

Regardless of waveform configuration, the slope of the input voltage ramp determines the intensity or amplitude of the electric field developed through the MUT during the constant field period, e.g., steeply sloped input ramps generate electric fields with greater intensity than input ramps with more gradual or lower slopes. Conversely, it is the period of the input voltage ramp that determines the duration of the constant intensity field period, e.g., longer input ramp periods generate electric fields with greater duration than input ramps with shorter periods. For any given input ramp segment, unipolar starting from zero volts to some peak applied voltage, or bipolar starting from some peak applied voltage to another peak voltage of opposite polarity, either the ramp slope or peak applied voltage can be manipulated by electronic methods, such as programing the power supply, to control field intensity versus field exposure time. This engineering control method provides a means to tailor field intensity versus field exposure time to better perform with different materials under treatment, different organisms or tissue types, or different operating conditions such as the temperature of a MUT.

However, the method of electronically manipulating the input waveform, e.g. by programming the power supply, has some constraints within certain limits. Input ramp slope and ramp period are inversely correlated, that is, increasing ramp slope proportionally decreases ramp period and vice versa. Since field intensity is determined by input ramp slope, and field exposure time is determined by input ramp period, said intensity and exposure time are also inversely correlated when electronically manipulated. The extent to which field intensity and field exposure time can be changed is determined by the peak or maximum applied voltage, which is limited for any given breakdown strength and thickness of a particular dielectric barrier material.

Figure 10:
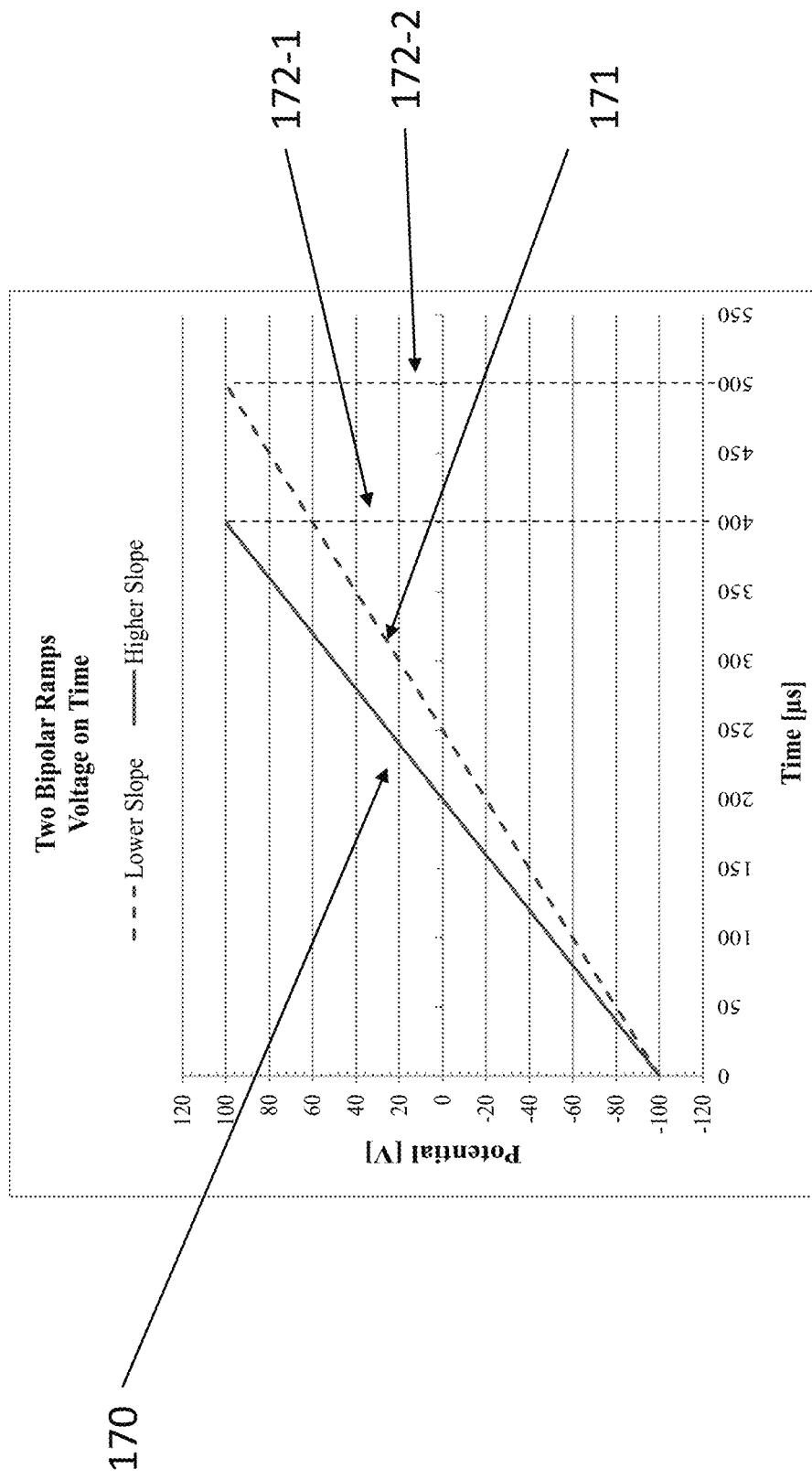
FIG. 10 illustrates a chart detailing a comparison of two bipolar linear voltage input ramps of the type usable with the embodiments of the present invention.

Since the dielectric breakdown strength and thickness of a barrier material determine the peak voltage that can be safely applied to the electrodes, the extent to which either field intensity or field exposure time can be increased is limited. For example, if barrier material breakdown strength (either field stress or time dependent) limits the peak applied potential to 100 volts, when an input ramp with a slope designed for a particular field intensity reaches that peak voltage limit, the ramp period cannot be made longer, thus limiting the maximum field exposure time for that field intensity. Conversely, when an input ramp with a period designed for a particular field exposure time reaches the same 100-volt limit, the ramp slope cannot be made greater (steeper), thus limiting the maximum field intensity during that ramp period. FIG. 10 compares two input linear voltage ramps for the embodiments of the present invention: one with a high slope (steep) 170 having a 400 µs period and another with a lower slope (more gradual) 171 having a 500 µs period. Both ramps 170, 171 are limited to a peak potential of +/−100 volts. The vertical dotted lines 172-1, 172-2 indicate the ramp periods. Given the +/−100 peak voltage limit, the steeper slope can generate a field intensity of 35 kV/cm, but can only do so for 400 µs, while the more gradual sloped ramp can only generate a field intensity of 25 kV/cm, but can do so for a longer period, 500 µs. Although this engineering control method for manipulating field intensity versus field exposure time is limited in this regard, other control methods previously explained in this disclosure can expand or extend this limitation. One method is by increasing electrode area or number of electrodes 100 while proportionally increasing barrier thickness. This method increases the peak voltage that can be safely applied to the electrodes 100, which in turn increases the extent to which any combination of field intensity and exposure time can be increased. If this engineering control method was applied to the example illustrated in FIG. 10, the upper limit of field intensity and field exposure time are increased for both input voltage ramps shown. This design control method expands the extent to which field intensity and exposure time can be controlled by the method of electrically manipulating ramp slope alone.

Equation (3) defines the relationship between all of the system parameters required to employ all of the engineering control methods of the embodiments of the present invention as disclosed herein. The first term m in equation (3) denotes input ramp slope, which is expanded in the second term as $(\hat{\varphi}_a/t_r)$ to show the peak input voltage over the input ramp period. Since the input voltage ramp is linear with respect to time, i.e., $dv/dt=m$ where m is a constant, $dv/dt$ always equals $(\hat{\varphi}/t_r)$. Since the last expression on the right side of equation (3) defines the value of m, equation (3) demonstrates the inverse correlation between peak applied voltage $\hat{\varphi}_a$ and input ramp period $(t_r)$, which in turn defines the engineering control space within which ramp slope m (that determines field intensity) and ramp period $(t_r)$ (that determines field exposure time) can be electronically manipulated, e.g., by programming the power supply. For example, if the quotient $(\hat{\varphi}_a/t_r)$ has a value of 2 as quantified by the expression on the right side of equation (3), then peak applied voltage and ramp period can only be electronically manipulated for any two respective values of $(\hat{\varphi}_a)$ and $(t_r)$ that have a quotient value of 2, e.g., 50 for peak applied voltage (which determines field intensity) and 25 for ramp period (which determines field exposure time), 80 for peak voltage and 40 for ramp period, etc. (these are fictitious values for demonstration purposes only). To wit:

$$m = \frac{\hat{\varphi}_a}{t_r} = E_s \frac{\sigma_s}{\varepsilon_d} \frac{A_s}{A_d} 2 d_d \qquad (3)$$

where $(E_s)$ and $(t_r)$ denote field intensity and ramp period respectively, $(\hat{\varphi}_a)$ is peak applied potential in volts, $(\varepsilon_d)$ is the absolute permittivity of the dielectric barrier material, $(\sigma_S)$ denotes the electrical conductivity of the MUT, $(A_d)$ and $(A_s)$ denote the area of the electrode(s) 100 in one flow manifold A or B (regardless of polarity) and the cross-sectional area of the MUT respectively (the cross-sectional area of the connecting tube 102 when configured for processing/treating fluids or said space between the electrodes 100 when configured for treating a solid MUT, and $(d_d)$ is the thickness of the dielectric barrier material that coats the conductive substrate of the electrode(s) 100 illustrated in FIG. 1A.

Referring to equation (3), the embodiments detailed below are provided as an aid to the person skilled in the pertinent arts for understanding and appreciating the range and benefits of the systems and methods disclosed and claimed herein.

One embodiment of the present invention comprises arranging the electrodes 100 and flow manifolds A and B with respect to the conveyance connection tube 102 or space accommodating a solid MUT in such a manner to align the electric field vector parallel with/to the flow direction or solid orientation of the MUT, while still making or otherwise forming a series capacitive network comprised of the electrodes 100 and MUT.

Another embodiment of the present invention comprises voltage or current sourcing the electrodes 100 with time variant linear or quasilinear voltage or current input ramps to generate electric fields through (in) materials under treatment that comprise constant or quasi-constant field intensity.

Another embodiment of the present invention comprises electronically controlling field intensity $(E_s)$ versus field exposure time $(t_r)$ by means of programming or selecting the slope m of the input voltage ramp from the power supply. This embodiment is useful for tailoring said intensity and exposure time to suit the electrical conductivity $(\sigma_s)$ of a particular MUT, a particular electric field effect, or a particular operating condition. This embodiment is limited by the peak voltage $(\hat{\varphi}_a)$ that can be safety applied to the dielectric barrier material and is constrained by the inverse correlation between input voltage ramp slope m and ramp period $(t_r)$ as illustrated in FIG. 10.

Another embodiment of the present invention comprises manipulating the area of the electrode(s) $(A_d)$ 100 to change electrode capacitance without having to change barrier thickness $(d_d)$ or the dimensions of the MUT (d) or $(A_s)$ and therefore without changing the peak applied voltage limit $(\hat{\varphi}_a)$ imposed by barrier material breakdown strength, process flow rate (fluid), physical size (solid), or the electrical conductivity $(\sigma_s)$ of a MUT (such as materials that have high conductivity). This embodiment is useful for controlling said intensity and exposure time to suit any MUT, organism or tissue, desired electric field effect, or operating condition. This embodiment is also useful for compensating for the poor performance of dielectric barrier materials that may have low permittivity $(\varepsilon_d)$ but otherwise have high performance material properties such as high dielectric breakdown strength, high volume resistivity, robust resistance to cleaning chemicals, food safety, etc. This embodiment is also useful for scaling the system for any process flow rate regardless of the permittivity $(\varepsilon_d)$ of the dielectric barrier material employed. Since the area of the electrodes $(A_d)$ can be manipulated without having to change the area of the MUT $(A_s)$ barrier thickness $(d_d)$ or the permittivity of the barrier dielectric material $(E_d)$ this method has no practical or theoretical limits relative to achieving any desired electric field effect or process flow rate. This embodiment also has no practical or theoretical limits relative to the electrical conductivity of any material under treatment or being processed.

Another embodiment of the present invention comprises manipulating the thickness of the dielectric barrier $(d_d)$ to change electrode capacitance or peak applied voltage $(\hat{\varphi}_a)$ without having to change the area of the electrodes $(A_d)$ or the dimensions of the MUT (fluid or solid) $(d_s)$ or $(A_s)$. This embodiment is useful for increasing said intensity and exposure time to suit any MUT, organism or tissue, desired electric field effect, or operating condition by decreasing said barrier thickness $(d_d)$. This embodiment is also useful for increasing the peak voltage limit $(\hat{\varphi}_a)$ imposed by barrier materials that have low dielectric breakdown strength, but otherwise have high performance material properties such as high permittivity $(\varepsilon_d)$, high volume resistivity, good food safety, etc., thereby increasing the upper limits for said intensity and exposure time by means of increasing barrier thickness $(d_d)$.

Another embodiment of the present invention comprises increasing the length $(d_s)$ of the MUT, i.e., by increasing connecting tube 102 if treating a fluid, or by increasing said space $(d_s)$ if treating a solid, to increase the electrical resistance of a MUT, thereby compensating for high conductivity fluids or solids under treatment that would otherwise result in high system current and excessive heating (excessive temperature rise). This embodiment is also useful to decrease conduction current through the electrode barriers, thus further reducing electrochemical byproducts and electrolysis, and thereby compensating for poor performing dielectric materials that may have low volume resistivity, but otherwise have high performance material properties such as high dielectric breakdown strength, high permittivity $\varepsilon_d$, robust resistance to cleaning chemicals, etc. This embodiment is also useful for increasing said field exposure time for any given field intensity or process flow rate (fluid) without having to change electrode area $(A_d)$, barrier thickness $(d_d)$, ramp slope (m), or peak applied potential $(\hat{\varphi}_a)$. Since increasing the length $(d_s)$ of the MUT does not change field intensity $(E_s)$ for any given electrode area $(A_d)$ barrier thickness $(d_d)$ or dielectric barrier material, this embodiment has no practical or theoretical limits with regard to achieving any desired electric field effect or process flow rate.

Another embodiment of the present invention comprises manipulating the area $(A_s)$ of the MUT to change field intensity $(E_S)$ within the MUT without having to change the area of the electrode(s) $(A_d)$ 100, and therefore without having to change device capacitance, system current, barrier thickness $d_d$, or dielectric barrier material for any desired electric field intensity or field exposure time. This embodiment is useful for treating or otherwise processing a material that has high electrical conductivity, such as milk, fruit juice, sea water, etc., that would otherwise require high system current, employment of a dielectric barrier material with higher permittivity ($\varepsilon_d$), thinner electrode barriers ($d_d$), or higher applied voltage ($\hat{\varphi}_a$) for any given electric field intensity and/or any given field exposure time. This embodiment is also useful for accommodating different materials under treatment that have diverse electrical conductivities, such as one fruit juice versus a different fruit juice, by replacing one connecting tube 102 with another tube having a different cross-sectional area ($A_s$), without having to change any other operating or design parameter including system current, peak applied voltage ($\hat{\varphi}_a$), electrode area ($A_d$), barrier thickness ($d_d$), dielectric barrier material, or flow rate. This embodiment is also useful for applying different field intensities to the MUT during the entire period of field exposure by means of installing a connection tube 102 having different areas ($A_s$) at different locations along its length ($d_s$), for example by increasing tube 102 area ($A_s$) from the inlet end to the outlet end between flow manifolds A and B, or the reverse with respect to fluid flow. This embodiment provides a means to progressively vary field intensity and field exposure time, such as a stepwise increase or decrease respectively, thereby tailoring intensity and exposure time to better suit any MUT, organism or tissue, desired electric field effect, or operating condition.

It is the combination of separation of the fluid pathway or occupied solid from the electrodes by a connection tube or space, parallel alignment of the electric field vector with said flow direction or solid orientation of the MUT, and the generation of constant intensity electric fields by means of linear voltage ramped input waveforms, that provide the means to independently manipulate electrode and MUT area, MUT length, barrier thickness, peak applied potential, and ramp period, which in turn provides independent engineering or design control over field intensity and field exposure time regardless of dielectric barrier or MUT material properties. These material properties include barrier permittivity, breakdown strength, and volume resistivity, as well as MUT conductivity, permittivity, phase, viscosity, flow rate (if fluid), size (if solid), and the physical size of suspended, entrained, or embedded particles in the MUT.

As used herein, "materials under treatment" (MUT) means any material subjected or exposed to the electric fields generated by the embodiments of the present invention for causing an electric field effect in said material. The material may be a fluid in gas or liquid phase, or a solid phase material. "Electrically insulated electrodes" means a device functioning as an element comprised of an electrically conductive substrate that is coated by or otherwise covered on one side with a dielectric material that has desirable material properties such as barrier functions against electronic and ionic conduction current, i.e., electronic and ionic resistivity, polarizability when exposed to an electric field, i.e., electric permittivity, and resistance to electric field stress, time dependent, and charge injection type dielectric breakdown mechanisms, i.e., breakdown strength, thus electrically insulating said conductive substrate from the material under treatment. The term "barrier thickness" refers to the thickness of the dielectric coating on one side of the electrically conductive substrate. The term "dielectric barrier material" or "dielectric barrier" refers to the dielectric material coating one side of said electrically conductive substrate. Said substrate is connected by wires or other conductive conveyance to a source of electricity, such as a power supply, that supplies electric energy or power to said electrodes. The terms "linear voltage or current ramp," and "quasilinear voltage or current ramp," refer to types of input waveforms that electrically source or power said electrically insulated electrodes, one comprising a voltage source to the electrodes, the other comprising a current source to the electrodes, and both comprised of time variant input voltage ramps that are either linear with respect to time, i.e., $dv/dt=m$ where m is a constant, or quasilinear, i.e., $dv/dt=m+A\cdot e^{-t/\tau}$, where m is a constant, A is the quotient of system current over system capacitance, and ($\tau$) is device RC time constant. The term "sourcing" is an electronic engineering term meaning supplying electric energy to said electrodes, or with respect to time, supplying electric power to said electrodes. Electric fields that are generated "through" a material also reside in that material to an extent proportional to that material's absolute permittivity and the intensity of said field. The term "tube" is used interchangeably with pipe, conduit, duct, or any means of conveying or otherwise transporting a gas or liquid phase fluid from one place to another. The term "cross-sectional area" means the area plane of any element or material that is perpendicular to the electric field vector generated by the embodiments of the present invention.

Although the invention has been described in detail with reference to several embodiments, additional variations and modifications exist within the scope and spirit of the invention as described and defined in the following claims.

I claim:

1. A method for generating an electric field comprising:
positioning one or more groups of two electrically insulated electrodes in a spaced relationship wherein each of said one or more groups of two electrically insulated electrodes comprise a first electrode having a polarity opposite that of a second associated electrode;
causing a fluid material to flow, or a solid material to be positioned, between said one or more groups of two electrically insulated electrodes;
applying a time variant input, quasilinear voltage or current ramp input waveform to said one or more groups of two electrically insulated electrodes; and
aligning an electric field vector generated by said one or more groups of two electrically insulated electrodes and said time variant input, quasilinear voltage or current ramp input waveform geometrically parallel with (i) a flow direction of said fluid material under treatment or (ii) a direction of a highest permittivity axis of said solid material under treatment.

2. The method for generating an electric field of claim 1 further comprising:
applying the time variant quasilinear voltage or current ramp input waveform to generate an electric field having a constant or quasi-constant field intensity relative to time through said fluid material under treatment or in said solid material under treatment.

3. The method for generating an electric field of claim 2 further comprising:
manipulating electric field intensity during one or more ramp periods of said time variant quasilinear voltage or current ramp input waveform by varying a slope of said input ramp.

4. The method for generating an electric field of claim 2 further comprising:
manipulating electric field exposure time during one or more ramp periods of said time variant quasilinear voltage or current ramp input waveform by varying a ramp period of said input ramp.

5. The method for generating an electric field of claim 1 further comprising:

manipulating electric field intensity by separating said electrodes from said fluid material under treatment with a conveyance connecting tube such that an area of said electrodes can be manipulated without changing the cross-sectional area of said fluid material under treatment flowing within said conveyance connecting tube.

6. The method for generating an electric field of claim 1 further comprising:
manipulating electric field exposure time by separating said electrodes from said solid material under treatment by a pre-established space such that an area of said electrodes can be manipulated without changing the cross-sectional area of said solid material under treatment within said pre-established space.

7. The method for generating an electric field of claim 1 further comprising:
coating said electrically insulated electrodes with a low permittivity dielectric material; and
separating said electrodes from said fluid material under treatment with a conveyance connecting tube such that an area of said electrodes can be manipulated without changing a peak applied voltage, dielectric material coating thickness or cross-sectional area of said fluid material under treatment flowing within said conveyance connecting tube.

8. The method for generating an electric field of claim 1 further comprising:
coating said electrically insulated electrodes with a low permittivity dielectric material; and
separating said electrodes from a solid material under treatment by a pre-established space such that an area of said electrodes can be manipulated without changing a peak applied voltage, dielectric material coating thickness or cross-sectional area of said solid material under treatment within said pre-established space.

9. The method for generating an electric field of claim 1 further comprising:
coating said electrically insulated electrodes with a low breakdown strength dielectric material;
separating said electrodes from said fluid material under treatment with a conveyance connecting tube;
manipulating a thickness of said dielectric material;
manipulating a peak applied voltage proportional to said manipulating said thickness of said dielectric material coating; and
manipulating an area of said electrodes proportional to said manipulating said peak applied voltage and proportional to said manipulating said thickness of said dielectric material without changing a cross-sectional area of said fluid material under treatment flowing within said conveyance connecting tube.

10. The method for generating an electric field of claim 1 further comprising:
coating said electrically insulated electrodes with a low breakdown strength dielectric material;
separating said electrodes from solid material under treatment by a pre-established defined space;
manipulating a thickness of said dielectric material;
manipulating a peak applied voltage source proportional to said manipulating said thickness of said dielectric material; and
manipulating an area of said electrodes proportional to said manipulating said peak applied voltage source and to said manipulating said thickness of said dielectric material coating without changing a cross-sectional area of said solid material under treatment within said pre-established defined space.

11. The method for generating an electric field of claim 1 further comprising:
coating said electrically insulated electrodes with a low volume electrical resistivity dielectric material; and
separating said electrodes from said fluid material under treatment with a conveyance connecting tube such that a length of said conveyance connecting tube can be manipulated without changing an area of said electrodes, a cross-sectional area of said material under treatment or said conveyance connecting tube, a thickness of said dielectric material coating or a peak applied voltage.

12. The method for generating an electric field of claim 1 further comprising:
coating said electrically insulated electrodes with a low volume electrical resistivity dielectric material; and
separating said electrodes from said fluid material under treatment by a pre-established space such that a length of said space can be manipulated without changing an area of said electrodes, a cross-sectional area of said material under treatment or said pre-established space, a thickness of said dielectric material coating or a peak applied voltage.

\* \* \* \* \*